(12) United States Patent
Ohnesorge et al.

(10) Patent No.: US 6,400,790 B1
(45) Date of Patent: Jun. 4, 2002

(54) METHOD FOR IMAGE RECONSTRUCTION FOR A CT APPARATUS AND CT APPARATUS FOR THE IMPLEMENTATION OF SUCH A METHOD

(75) Inventors: Bernd Ohnesorge, Erlangen; Thomas Flohr, Uehlfeld, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/450,388

(22) Filed: Nov. 29, 1999

(30) Foreign Application Priority Data

Nov. 27, 1998 (DE) .......................................... 198 54 947

(51) Int. Cl.⁷ ................................................ A61B 6/03
(52) U.S. Cl. .............................. 378/15; 378/4; 378/901
(58) Field of Search ............................ 378/4, 8, 15, 19, 378/901

(56) References Cited

U.S. PATENT DOCUMENTS

| | | | | |
|---|---|---|---|---|
| 5,291,402 A | * | 3/1994 | Pfoh | 378/13 |
| 5,377,250 A | * | 12/1994 | Hu | 378/15 |
| 5,430,783 A | * | 7/1995 | Hu et al. | 378/4 |
| 5,559,847 A | * | 9/1996 | Hu et al. | 378/4 |
| 5,682,414 A | | 10/1997 | Saito | 378/146 |
| 5,974,108 A | * | 10/1999 | Taguchi et al. | 378/4 |
| 6,243,438 B1 | * | 6/2001 | Nahaliel et al. | 378/4 |

FOREIGN PATENT DOCUMENTS

DE     OS 42 24 249     1/1993

\* cited by examiner

*Primary Examiner*—David V. Bruce
(74) *Attorney, Agent, or Firm*—Schiff Hardin & Waite

(57) ABSTRACT

In a method for image reconstruction for a CT apparatus and CT apparatus for the implementation of such a method, acquisition of the data underlying an image reconstruction for an image plane at a specific position on the system axis ensues by combining measured values, for each individual projection angle needed for this image reconstruction, that are registered exclusively for this projection angle with different lines of detector elements, to form data apparently registered with a detector having only one line of detector elements, with a weighting of the measured values ensuing. The image reconstruction is then undertaken using a conventional algorithm for operating on data from a detector having only one line of detector elements.

24 Claims, 12 Drawing Sheets

METHOD FOR IMAGE RECONSTRUCTION FOR A CT APPARATUS AND CT APPARATUS FOR THE IMPLEMENTATION OF SUCH A METHOD

BACKGROUND OF THE INVENTION

1. Field of the Invention

The present invention is directed to a method for image reconstruction in a computed tomography (CT) apparatus, such as a spiral CT apparatus, as well as to a CT apparatus, such as a spiral CT apparatus, for implementing the method.

2. Description of the Prior Art

A spiral CT (computed tomography) apparatus having a radiation source movable around an examination subject from which a fan-shaped ray beam emanates, and having a detector with a number of lines of detector elements (detector lines) that receives the fan-shaped ray beam, wherein the examination subject and the detector are displaceable relative to one another in the direction of the system axis for the implementation of an examination. It is known to operate such a system to register a number of projections each with several lines of detector elements for a number of projection angles and positions along the system axis, wherein the same lines of detector elements are employed for the registration of all projections. An image is reconstructed from the registered projections.

CT systems of this type are disclosed, for example, in German OS 196 47 435, U.S. Pat. No. 5,682,414 and German OS 42 24 249 as well as U.S. Pat. No. 5,291,402.

For spiral exposures with a CT apparatus that has a detector with a single line of detector elements, an interpolation between the measured values lying in front of and behind the image plane is implemented for generating projections in the desired image plane for each projection angle.

Two interpolation methods are currently most common. In the first, a linear interpolation is undertaken between two measured projections lying closest to the image plane, these having been registered at the same projection angle α but in different revolutions. This type of interpolation is referred to as 360LI interpolation. In the second method, interpolation is carried out between two sets of measured values lying closest to the image plane, one set of these values having been registered at the projection angle $\alpha_d$, the other set at the projection angle $\alpha_{c'}$, complementary thereto. The relation $\alpha_{c'}=\alpha_d \pm \Pi$ applies for th e central channel of the detector. This type of interpolation is referred to as 180LI interpolations. It supplies narrower effective slice widths (characterized, for example, by the full width at half-maximum FWHM) than the 360Ll interpolation given the same pitch. As a tradeoff, the image noise is increased compared to 360LI interpolation given the same output power of the X-ray tube (same mA value) and the artifact susceptibility is greater. Both types of interpolation are schematically illustrated in FIG. 1, which shows the projection angle α as a function of the detector position in the z-direction during a spiral scan for the pitch p=2 normalized onto the collimated width d of a line of detector elements of the detector, i.e. the collimated slice thickness.

In a CT apparatus having multi-line detectors, the reconstruction of spiral data with exact and approximative methods described in German PS 196 14 223 that in fact take the exact geometry into consideration, but this is very calculation-intensive and therefore is not particularly suited for use in a commercial CT apparatus.

For low line numbers M (for example, M≦5), the angle of inclination—also referred to as the cone angle—of the X-rays (referred to as measuring rays) incident onto the detector relative to a plane perpendicular to the z-axis of the CT apparatus (also referred to as the system axis) can be neglected for reducing the calculating outlay, and the 180LI and 360LI interpolations that are standard for a CT apparatus with a detector having only one line of detector elements can be transferred to multiple detector lines. This is the reconstruction method that is employed in the 2-line CT scanner "Elscint Twin" (see "Dual-slice versus single-slice spiral scanning: Comparison of the physical performances of two computed tomography scanners", Yun Liang and Robert A. Kruger, Med. Phys. 23(2), Febuary 1996, pp. 205–220).

In a presentation analogous to FIG. 1, the principle of the 180LI and 360LI interpolation transferred onto a number of lines is shown in FIG. 2 for the pitch p=3 with reference to the arbitrarily selected example of a CT apparatus having a detector with four lines of detector elements. The pitch p is the feed in z-direction per revolution of the radiation source with reference to the collimated width d of a line of detector elements of the detector, i.e. the collimated slice thickness. The basic problems in the standard multi-line spiral interpolation become clear from FIG. 2:

First, in order to generate data for a predetermined projection angle by interpolation, these data corresponding to a corresponding projection in the desired image plane acquired with a detector having only one line of detector elements, the contribution of a number of projections from different revolutions of the spiral scan must be taken into consideration. The interpolation weightings for a specific projection are thus dependent on the z-position of other projections. Given realization on a computer, this makes the processing of the individual projections more difficult. Dependent on the pitch p, moreover, multiple scans occur (in FIG. 2, for example, at line 1 and line 4 that scan the same z-positions in successive revolutions), which have to be taken into consideration in the calculation of the interpolation s weightings, making the interpolation more computationally complicated.

Second given pitch values p≧M (M is the number of lines of the detector), a 180LI interpolation must be implemented if the slice sensitivity profile is not to spread unacceptably. For illustration, the full wave at half-maximum FWHM of the slice sensitivity profile occurring given 180LI and 360LI interpolation as function of the pitch value p is shown in FIG. 3 for the example of the detector having four lines of detector elements.

180LI interpolation given a detector with one line of detector elements means that interpolation is generally carried out between a direct ray and the ray complementary thereto. The situation is more complicated given a detector having a number of lines. In that case, 180LI interpolation means that interpolation is always carried out between the two measured values that lie closest to the image plane. Dependent on the pitch value p and the position of the image plane in the z-direction, interpolation for a specific projection angle α is carried out either between direct measured values, namely when these lie closer to the image plane, or between a direct measured value and a measured value complementary thereto when these lie closer to the measured plane.

When, however, interpolation is carried out between direct and complementary measured values given a projection angle $\alpha_d$, the complementary measured value at $\beta_c=-\beta_d$ must be found for every measured value identified by th e direct projection angle $\alpha_d$ and the corresponding fan angle $\beta_d$. The projection angles $\alpha_d$ and $\alpha_c$ of direct and complementary projections are offset by exactly 180° only in the rotational center, i.e. for $\beta_d=\beta_c=0$. The relations $$\beta_c = -\beta_d$$

$$\alpha_c = \alpha_d + 2\beta + \Pi \tag{1}$$

apply in the general case, i.e. the complementary measured value at $\beta_c$ for each direct measured value characterized by the projection angle $\alpha_d$ and the fan angle $\beta_d$, is from a different projection, that accordingly was registered at a different z-position. Interpolation weightings that are independent of fan angle therefore must be used in the 180LI interpolation, and the contributions of different complementary projections for each direct projection must be considered, this immensely increasing the calculating outlay.

Third, the standard deviation of the pixel noise measured in the image arises from the quadratic sum of all interpolation weightings for each pitch value p. These interpolation weightings are pitch-dependent in the 180LI and in the 360LI interpolations. Given a fixed output power of the X-ray tube, the pixel noise to be set for each pitch value p is thus also defined. This pixel noise exhibits unexpected and unwanted dependencies on the pitch p. For a detector having four lines of detector elements, for example, the measured values of all four detector lines fall onto the same z-positions in successive revolutions given the pitch p=1. They can therefore be simply averaged before the interpolation. As a result, a dose accumulation by the a factor of four, and therefore a halving of the pixel noise, occur compared to a detector having only one line of detector elements. When the pitch is increased only slightly, for example to p=1.1, this multiple scan is eliminated. A narrower slice sensitivity profile is then obtained in the 180LI and the 360LI interpolations, but at the cost of the same pixel noise as in a one line detector.

With conventional 180LI and 360LI interpolations, it is not possible given low pitch values (for example, p=1.1, as above), to utilize the overlapping scanning in the z-direction (i.e., the lines of the detector successively acquire the same z-region in different revolutions) for the purpose of reducing the pixel noise. In particular, it is also not possible to employ only a freely selectable part of the data available overall at the z-position $Z_{ima}$ (the index "ima" stands for image) for the reconstruction. It is thus also not possible to set a freely selectable compromise between reduced pixel noise(on the basis of the overlapping scanning) and improved time resolution of the reconstruction.

SUMMARY OF THE INVENTION

An object of the present invention is to provide a method of the type initially described that is improved in terms of the slice sensitivity profile as well as a spiral CT apparatus for the implementation of such a method.

The above object is achieved in accordance with the principles of the present invention in a method for image reconstruction for a CT apparatus, and in a CT apparatus for implementing the method, wherein acquisition of the data needed for an image reconstruction of an image plane at a specific position in the system axis ensues by combining measured values for each individual projection angle needed for the image reconstruction, that are registered exclusively for this projection angle with different lines of detector elements, to form data apparently registered with a detector having only one line of detector elements, by conducting a weighting of the measured values for the projections which enter into the image reconstruction. The image reconstruction is then conducted using an algorithm for operating on data from a detector having only one line of detector elements.

The invention thus combines weightings undertaken independently of one another for the individual projections with an algorithm conventionally employed for a detector having only one line of detector elements for the image reconstruction. The inventive method has the following advantages:

First, the weighting referred to below as spiral weighting is undertaken separately for each projection angle for the projections registered with the individual lines of detector elements of the detector, called multi-line projection below. Differing from the conventional 180LI or 360LI interpolation, the z-position of projections that were acquired at other projection angles, plays no part in the calculation of the weightings for the individual projections of a multi-line projection (spiral weightings) at the projection angle $\alpha$. The processing of the individual projections can thus quite simply ensue sequentially.

Secondly, the spiral weighting is undertaken in fan data. For each line i of the detector, the interpolation weighting for each projection $\alpha$ is dependent on its z-position and on the z-position of the desired image. By contrast or 180Li interpolation, however, it is independent of the fan angle $\beta$. Differing from 360LI interpolation, however, the slice sensitivity profile of the inventive method remains acceptably narrow up to the pitch value p=2M. The artefact susceptibility of the inventive method is comparable to that of 180LI interpolation.

Third, given small values of the pitch p with overlapping scanning in the z-direction, the region of the projection angle contributing to the image can be arbitrarily selected within certain limits. Without limitation in the image quality, any desired compromise between improved dose utilization and reduced pixel noise (due to the overlapping scanning) and improved time resolution of the reconstruction thus can be set.

The reason why these advantages can be achieved shall be explained below:

When it is established as a condition, that a full wave at half-maximum FWHM of the slice sensitivity profile is to be achieved that corresponds to that of a 360LI interpolation given the pitch 1, i.e. that remains smaller than approximately 1.3 times the collimated width of a detector line (FWHM≦1.3 d), then a 180LI interpolation must be employed in known methods given pitch values M≦p≦2M.

In order to achieve FWHM≦1.3d for M≦p≦2M, it is actually not necessary to unconditionally interpolate between the measured values that are the closest neighbors to the image plane, as occurs, however, in the 180LI interpolation. Instead, it would be adequate to interpolate exclusively between direct measured values in front of and behind the image plane as long as these are at no greater distance from one another than the width of a detector line, even when a complementary measured value lies closer to the image plane. With increasing pitch, however, the spacing of the available, direct measured values in the edge regions of the projection angle interval employed for the reconstruction becomes clearly greater than the width of a detector line because interpolation is no longer carried out between the measured values of the individual detector lines measured for the same projection angle. Instead, direct measured values offset by 360° from various revolutions must be employed. This explains the increase in the effective layer thickness and the considerable degradation of the slice profile given the 360LI interpolation wherein, of course, interpolation is only carried out between direct measured values (see FIG. 3). According to conventional methods, a complicated interpolation between direct and complementary measured values would have to be undertaken in these projection angle regions. In these critical projection angle regions, wherein an interpolation would be required between direct and complementary rays, the inventive method replaces this with the use of the direct rays by themselves. Inconsistencies at the boundaries of the reconstruction interval due to lacking interpolation can be effectively suppressed in the technique by a known transition weighting with an adequately smooth function that is undertaken in the subsequent overscan or sub-revolution reconstruction. In view of the artefact behavior, thus, this transition weighting replaces the lacking spiral interpolation.

In an embodiment of the invention, the image reconstruction can be undertaken both on the basis of a known sub-revolution reconstruction as well as on the basis of a known overscan reconstruction. In the case of a sub-revolution reconstruction, data are utilized that were acquired during a revolution angle of the radiation source of at most 2Π. In the case of an overscan reconstruction, a dataset is utilized that was acquired during a revolution angle of the radiation source of more than 2Π.

Independently of the type of image reconstruction, it is possible in the inventive method to undertake the combination of the data with respect to the projection angles to be taken into consideration such that a combination of direct and complementary measured values is not carried out, avoiding the disadvantages connected with this measure.

In a preferred embodiment of the invention, a combination of the data for the projection angles to be taken into consideration ensues sequentially, so that the outlay for an electronic computer for implementation of the inventive method is low.

An inventive spiral CT apparatus contains a parallel computer. The preferably sequential combination of the data can then ensue especially fast.

An inventive apparatus is a spiral CT apparatus wherein the region of the projection angles to be taken into consideration in the image reconstruction is freely selectable. Without limiting the image quality, it is then possible to realize any desired compromise between improved utilization of the x-ray dose and reduced pixel noise, and improved time resolution.

In an inventive spiral CT apparatus, the relative motion between examination subject and the radiation source and detector ensues with variable direction and/or variable speed. This is possible since only data that are derived from the same revolution of the radiation source are combined with respect to each projection angle.

DESCRIPTION OF THE PREFERRED EMBODIMENTS

Figure 4:
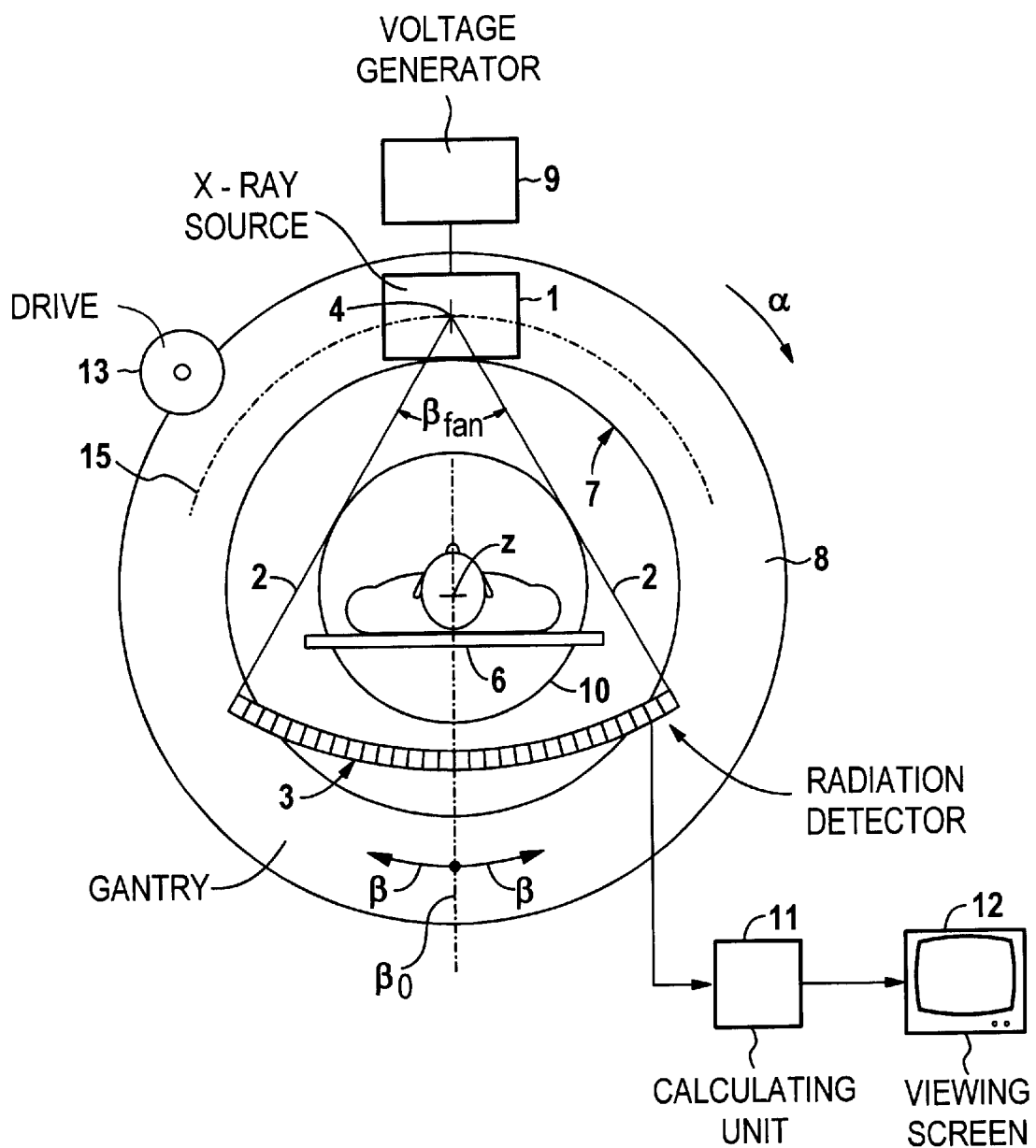
FIG. 4 shows a spiral CT apparatus operating according to the inventive method with a detector having four lines of detector elements.

The spiral CT apparatus shown in FIG. 4 has a measuring unit composed of an x-ray source 1, which emits a fan-shaped x-ray beam 2, and a detector 3, which is composed of a number of rows of detector elements, four rows of detector elements in the exemplary embodiment, for example having 512 detector elements each. The focus of the x-ray source 1 from which the x-ray beam emanates is referenced 4. The examination subject 5, a human patient in the exemplary embodiment, lies on a support table 6 that extends through the measuring opening 7 of a gantry 8.

The x-ray source 1 and the detector 3 are mounted to the gantry 8 lying opposite one another. The gantry 8 is rotatably seated around a z-axis of the CT apparatus referenced z that represents the system axis. For scanning the examination subject 5 in the α-direction, is rotated around the z-axis in the direction of the arrow referenced α, namely by an angle α that amounts to at least equal to 180° (Π) plus fan angle $\beta_{fan}$ (aperture angle of the fan-shaped x-ray beam 2). The x-ray beam 2 emanating from the x-ray source 1 operated with a voltage generator 9 thereby covers a measurement field 12 having a circular cross section. The focus 4 of the x-ray source 1 moves on a focus path 15 circularly curved around the rotational center lying on the z-axis.

Given predetermined angular positions of the measuring unit 1, 3, referred to as the projection angles, measured values are registered in the form of projections, whereby the corresponding measured values proceed from the detector 3 to an electronic computing unit 11 that reconstructs the attenuation coefficients of the picture elements of a picture element matrix from the sequences of measuring points corresponding to the projections and visually reproduces these on a viewing screen 12. Images of the transirradiated slices of the examination subject 5 thus are presented on the viewing screen 12.

Each projection is allocated to a specific angular position, i.e. a projection angle, and contains a number of measuring points corresponding to the number of detector elements, i.e. the channel number k, to which the corresponding measured value is allocated, with the respective channel being defined by the appertaining fan angle, which indicates the detector elements from which the respective measured value is derived. The fan angle $\beta_0$ is allocated to the middle channel, what is referred to as the central channel.

Since the detector 3 has a number of lines of detector elements, projections with respect to a number of slices of the examination subject 5 can be simultaneously registered as needed, with a number of projections corresponding to the number of active detector lines being registered per projection angle.

The drive 13 allocated to the gantry 8 can rotate the gantry 8 through a partial revolution or a complete revolution or an continuously rotate the gantry 8. A further drive is also provided that enables a relative displacement of the support table 6, and thus of the examination subject 5, relative to the gantry 8 with the measuring unit 1, 3, in the z-direction, so that as spiral scans can also be implemented, wherein spiral data are acquired. In the exemplary embodiment, not only a constant relative motion, i.e. a relative motion with constant direction and velocity, is possible, but also a non-constant relative motion, for example a periodic relative rotation with cosine-shaped curve of the velocity. The type of motion that is employed can be set with operating elements that are not shown in FIG. 4.

During the course of the image reconstruction, the electronic calculating unit 11, which can be parallel computer, implements, among other things, the following method steps:

(A) The spiral data of the M lines of detector elements present in the fan geometry are separately combined by addition for each projection angle $\alpha$ with weightings dependent on the projection angle $\alpha$, the line number i=1,2, . . . M, and the desired image position $z_{ima}$, so that a single-line projection arises for each $\alpha$, i.e. a projection as acquired with a detector having a single line of detector elements. The weightings for the multi-line projection given the projection angle $\alpha$, differing from the conventional 360 Ll or 180 LI interpolations, are not dependent on the z-position of other multi-line projections. The individual projections are therefore sequentially processed completely independently of one another.

(B) The weightings are pre-calculated and stored in the electronic calculating unit 11. The weightings increase linearly, for example, with decreasing distance of the detector lines from the desired image plane at $z_{ima}$. The projection angle ranges $\Delta\alpha_i$ needed for each of the M lines, overlap. The entire projection angle range $\Delta\alpha$ contributing to the image is freely selectable (with control elements not shown in FIG. 4) between the minimally required sub-revolution interval $$\Delta\alpha_{min}=\Pi+\beta_{fan}+\alpha_{trans} \quad (2)$$

(for example, $\Delta\alpha_{min}=4\Pi/3$)and a pitch-dependent maximum value $\Delta\alpha_{max}$ (for example, $\Delta\alpha_{max}=4\Pi$). $\beta_{fan}$ is the overall fan angle of the detector; $\alpha_{trans}$ is a transition angle that is additionally taken into consideration by means of a transfer function for reducing artifacts due to data inconsistencies between the starting and ending projection of the reconstruction.

(C) The single-line projections in the overall angular range $\Delta\alpha$ for $\Delta\alpha\leq 2\Pi$ are subjected to a conventional single-line sub-revolution reconstruction and are subjected to a conventional single-line overscan reconstruction for $\Delta\alpha>2\Pi$. Given a suitable selection of the transition angle $\Delta\alpha_{trans}$ and an adequately smooth transition weighting function, image artifacts due to data inconsistencies are effectively suppressed in both instances.

The inventive reconstruction method implemented by the electronic calculating unit 11 is described in detail below, without limitation of its universal validity, with reference to the example of the spiral CT apparatus according to FIG. 4 having a detector with four lines of detector elements (M=4). The comments, however, are analogously valid for other line numbers M>1. The adaptations needed for this purpose can be undertaken by a person skilled in the art without difficulty based on the information herein.

The inventive principle of spiral weighting, i.e. the weighted addition of the measured values of the individual detector lines i=1,2, . . . ,M with weightings dependent on the projection $\alpha$, on the line number i and on the desired image position $z_{ima}$, is explained with reference to the example of the four-line detector on the basis of FIGS. 5 through 10. This principle is initially explained for constant relative motion between examination subject, and the radiation source and the detector, as to direction and velocity.

A four-line spiral exposure given the pitch p for constant relative motion in z-direction is considered. An image is to be reconstructed at the z-position $z_{ima}$. The spiral weighting should yield a single-line data set that is subjected to a regular overscan (sub-revolution) reconstruction in the angular range $\Delta\alpha=\alpha_{RTD}$. $N_{RTD}$ multi-line projections are used.

Figure 5:
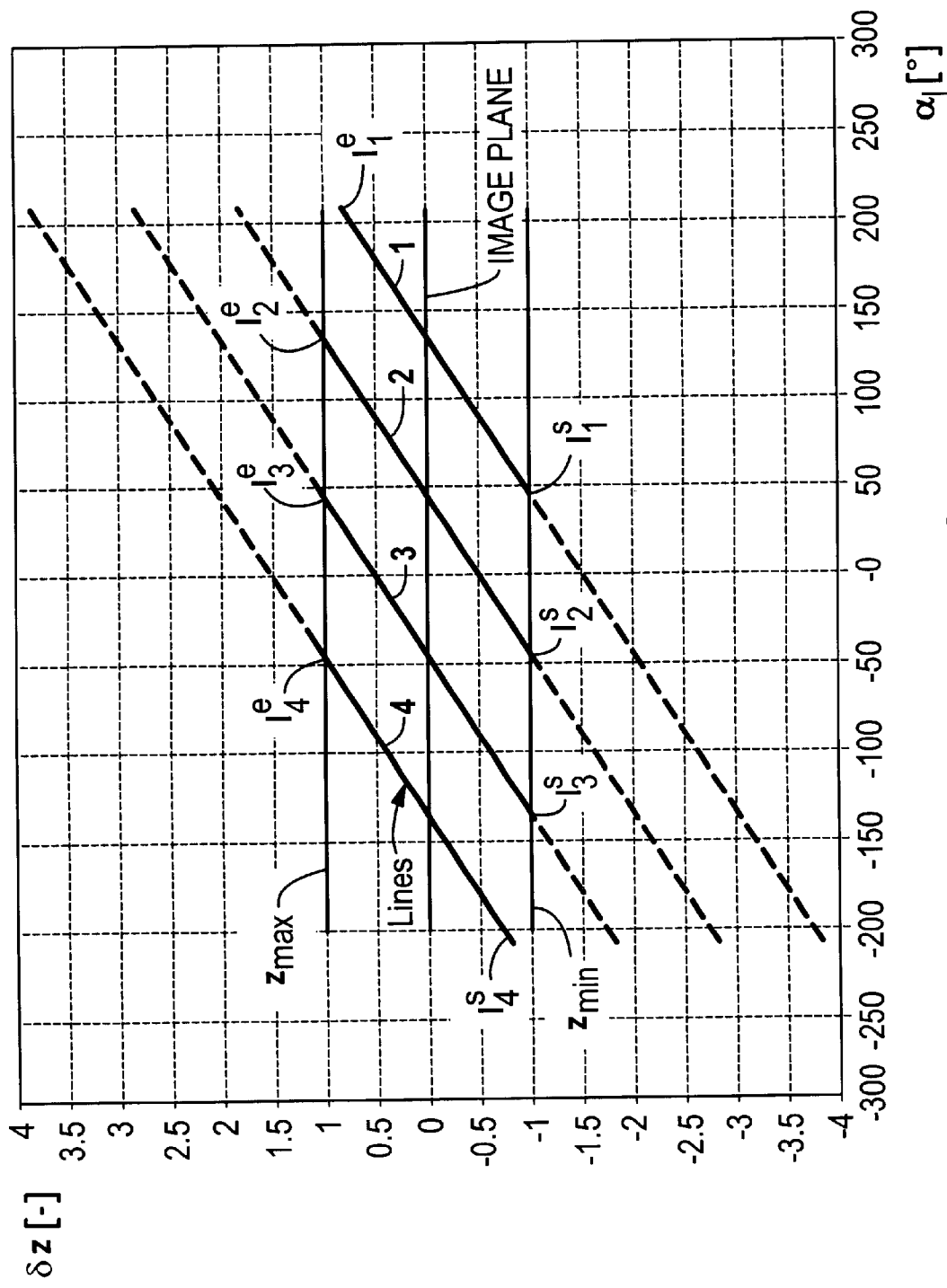
FIG. 5 is a diagram for the spiral CT apparatus of FIG. 4 illustrating the weighted combination of the data according to the inventive method.

Let $I^{ima}$ be that four-line projection for which the path of the focus intersects the image plane. For this projection, FIG. 5 illustrates the distance of the four detector lines from the image plane at the z-position $z_{ima}$ with reference to a collimated, i.e. effective width d of a detector line as function of the projection angle $\alpha_1$ for $-210°\leq\alpha_1\leq 210°$ for the pitch p=4 and an overscan reconstruction in the overall angular range $\Delta\alpha=\alpha_{over}=420°$, whereby $\alpha_1=0$ is that projection angle at which the path of the focus of the x-ray source intersects the image plane. Only measured values in a z-interval $z^{min}=z_{ima}-z\leq\Delta z\leq z^{max}=z_{ima}+\Delta z$ contribute for each detector line, this being illustrated by bold-face lines in FIG. 5. The corresponding measured values are weighted according to their distance from the image plane.

For the direction of the spiral (direction of the relative motion in z-direction), the z-distance $\delta z_i(I)$ o the M=4 detector lines i=1, . . .,4 from the image plane is $$\delta z_i(l) = \frac{(l-l^{ima})p}{N_{2\pi}} + i - \frac{M+1}{2} \quad (3)$$

with reference to the collimated width d of a detector line. M=4 is the number of detector lines. $N_{2\Pi}$, is the number of fan projections in a full revolution $2\Pi$. A corresponding equation derives for the opposite spiral direction.

Only data within a maximum distance $|\Delta z|$ from the image plane given $z_{ima}$ should contribute to the image for each of the M detector lines:

$$-\Delta z \leq \delta z_i(I) \leq \Delta z \quad (4)$$

that determines the projection range $[I_1^s, I_1^e]$, this being required for each line i.

The first line is an exception, whereby the last employed projection $I_1^e$ must be $$I_1^e = I^{ima} + \frac{N_{RTD}}{2} - 1 \quad (5)$$

even when $\delta z_1(I_1^e) > \Delta z$ applies and the last line M=4, for which the following start projection $I_4^s$ is required $$I_4^s = I^{ima} - \frac{N_{RTD}}{2} \quad (6)$$

as well as $\delta z_4(I_m^s) < -\Delta z$, since enough data must be available for the reconstruction angular range $\alpha_{TRD}$.

For all other instances, $I_i^s$ is calculated according to (3), with $\delta z_i(I_i^s) = -\Delta z$. The following thus derives:

$$I_i^s = I^{ima} - \left(\Delta z + i\frac{M+1}{2}\right)\frac{N_{2\pi}}{p} \quad (7)$$

Correspondingly, $$I_i^e = I^{ima} - \left(\Delta z - i + \frac{M+1}{2}\right)\frac{N_{2\pi}}{p} \quad (8)$$

is obtained for $\delta z_1(I_i^e) = -\Delta z$.
Then $$I_i^s = I^{ima} - \frac{N_{RTD}}{2} = I_4^s \quad (9)$$

$$I_i^e = I^{ima} + \frac{N_{RTD}}{2} - 1 = I_1^e \quad (10)$$

must be employed instead when, for small pitch values, $I_i^s$ or $I_i^e$ according to (7) and (8), exceed the selected reconstruction angular range $$\left[I^{ima} - \frac{N_{RTD}}{2}, I^{ima} + \frac{N_{RTD}}{2} - 1\right]$$

In summary, the following projection ranges are required for the weighted addition of the measured values of a four-line spiral data set given the pitch p when, subsequently, a single-line sub-revolution or overscan reconstruction is to be implemented in the angular range $\alpha_{TRD}$ ($N_{RTD}$ weighted single-line projections):

line 1

$$I_1^s = I^{ima} - (\Delta z - 1.5)\frac{N_{2\pi}}{p} \quad (11)$$

$$I_1^e = I^{ima} + \frac{N_{RTD}}{2} - 1$$

line 2

$$I_2^s = \max\left(I^{ima} - (\Delta z - 0.5)\frac{N_{2\pi}}{p}, I_4^s\right) \quad (12)$$

$$I_2^e = \min\left(I^{ima} + (\Delta z + 0.5)\frac{N_{2\pi}}{p}, I_1^e\right)$$

line 3

$$I_3^s = \max\left(I^{ima} - (\Delta z + 0.5)\frac{N_{2\pi}}{p}, I_4^s\right) \quad (13)$$

$$I_3^e = \min\left(I^{ima} + (\Delta z - 0.5)\frac{N_{2\pi}}{p}, I_1^e\right)$$

line 4

$$I_4^s = I^{ima} - \frac{N_{RTD}}{2} \quad (14)$$

$$I_4^e = I^{ima} + (\Delta z - 1.5)\frac{N_{2\pi}}{p}$$

This can clearly be expanded to M≠4.

For the simple case $\Delta z = 1$, one obtains line 1

$$I_1^s = I^{ima} + 0.5\frac{N_{2\pi}}{p} \quad (15)$$

$$I_1^e = I^{ima} + \frac{N_{RTD}}{2} - 1$$

line 2

$$I_2^s = \max\left(I^{ima} - 0.5\frac{N_{2\pi}}{p}, I_4^s\right) \quad (16)$$

$$I_2^e = \min\left(I^{ima} + 1.5\frac{N_{2\pi}}{p}, I_4^e\right)$$

line 3

$$I_3^s = \max\left(I^{ima} - 1.5\frac{N_{2\pi}}{p}, I_4^s\right) \quad (17)$$

$$I_3^e = \max\left(I^{ima} + 0.5\frac{N_{2\pi}}{p}, I_4^e\right)$$

line 4

$$I_4^s = I^{ima} - \frac{N_{RTD}}{2} \quad (18)$$

$$I_4^e = I^{ima} - 0.5\frac{N_{2\pi}}{p}$$

The spiral data $p_i(k, I)$ (k is the number of the detector channel) of each of the M detector lines i=1,2,...,M present in the fan geometry are weighted in the angular range a $[I_i^s, I_i^e]$ according to their distance $\delta z_i(I)$ from the image plane. The weightings $w_i(I)$ dependent on the projection angle $\alpha$ are thereby employed.

$$\sum_{i=1}^{M} w_i(I) = 1 \quad (19)$$

By contrast to the standard 180LI spiral interpolation, the weightings are not dependent on the channel number k.

As a simple example (without limitation of the universality), the simple case $\Delta z = 1$ with linear weighting functions $w_i(l)$ is considered. This has similarity with the standard 360LI interpolation within a freely selectable projection range, but surprising results deviating from the 360LI interpolation are obtained for the pixel noise and the slice sensitivity profile, particularly in the range $M \leq p \leq 2M$.

Given the four-line detector (M=4), the data from two detector lines i and i+1 contribute to the image (see FIG. 5) for each projection in the projection range $[I_3^s, I_2^e]$. In this projection angle range, the following weightings are assigned to the measured values $p_i(k,l)$ of every detector line i:

$$w_i = 1 - |\delta z_i(l)| = 1 - \left| \frac{(l - l^{ima})p}{N_{2\pi}} + i - \frac{M+1}{2} \right| \qquad (20)$$

$[I_i^s \leq I \leq I_i^e]$ is thereby in agreement with (19).

For $[I_4^s \leq I \leq I_3^s]$, only detector line 4 contributes to the image; only the detector line 1 contributes for $[I_2^e \leq I \leq I_4^e]$ (likewise see FIG. 5). $w_1(l)=/1$ must therefore be set for $[I_2^e \leq I \leq I_1^e]$ and $W_4(1)=1$ must be set for $[I_4^s \leq I \leq I_3^s]$, even when (in the case of high pitch values) the corresponding detector lines leave the z-range$\pm \Delta z$.

In summary, the following weightings are allocated to the spiral data $p_i(k,l)$ of the M=4 detector lines in the simple case $\Delta z=1$:

line 1

$$w_1(l) = 1 - \left| \frac{(l - l^{ima})p}{N_{2\pi}} - 1.5 \right| \text{ for } [l_1^s \leq l \leq l_2^s] \qquad (21)$$

$$w_1(l) = 1 \text{ for } [l_2^s \leq l \leq l_1^e]$$

line 2

$$w_2(l) = 1 - \left| \frac{(l - l^{ima})p}{N_{2\pi}} - 0.5 \right| \text{ for } [l_2^s \leq l \leq l_2^e] \qquad (22)$$

line 3

$$w_3(l) = 1 - \left| \frac{(l - l^{ima})p}{N_{2\pi}} + 0.5 \right| \text{ for } [l_3^s \leq l \leq l_3^e] \qquad (23)$$

line 4

$$w_4(l) = 1 \text{ for } [l_4^s \leq l \leq l_3^s] \qquad (24)$$

$$w_4(l) = 1 - \left| \frac{(l - l^{ima})p}{N_{2\pi}} + 1.5 \right| \text{ for } [l_3^s \leq l \leq l_4^e]$$

Figure 6:
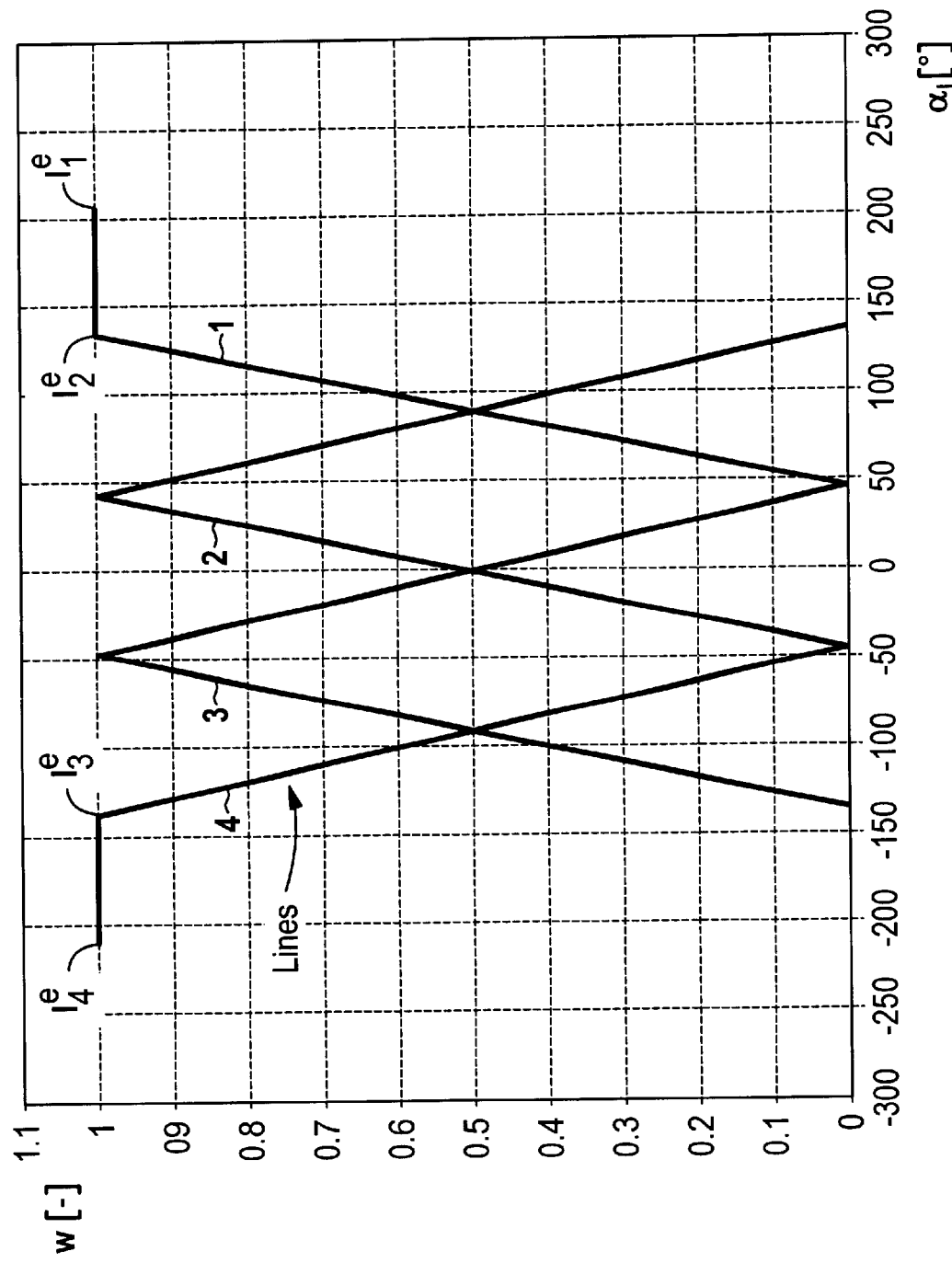
FIG. 6 is a diagram illustrating the weighting function applied in the combination of the measured values for the individual lines of the detector of the spiral CT apparatus according to FIG. 4 as a function of the projection angle.

As an example, the weighting functions $w_i(l)$ for pitch p=4, $\Delta z=1$ and $\alpha_{TRD}=420°$ (corresponding to FIG. 5) are shown in FIG. 6, whereby $\alpha l=0$ is again that projection angle at which the path of the focus of the X-ray source intersects the image plane.

With the weightings $w_i(l)$, a single-line dataset f(k,l) is calculated in fan geometry, this covering the projection region $$l^{ima} - \frac{N_{RTD}}{2} \leq l \leq l^{ima} + \frac{N_{RTD}}{2} - 1:$$

$$f(k,l) = p_4(k,l) \qquad \text{for } [l_4^s \leq l \leq l_3^s] \qquad (25)$$

$$f(k,l) = w_3(l)p_3(k,l) + w_4(l)p_4(k,l) \quad \text{for } [l_3^s \leq l \leq l_4^e]$$

$$f(k,l) = w_2(l)p_2(k,l) + w_3(l)p_3(k,l) \quad \text{for } [l_2^s \leq l \leq l_3^s]$$

$$f(k,l) = w_1(l)p_1(k,l) + w_2(l)p_2(k,l) \quad \text{for } [l_1^s \leq l \leq l_2^e]$$

$$f(k,l) = p_1(k,l) \qquad \text{for } [l_2^e \leq l \leq l_1^e]$$

This single-line fan dataset is subjected to a conventional single-line overscan or single-line sub-revolution reconstruction dependent on the reconstruction angle range. The smoothing overscan (sub-revolution) weighting effectively reduces line artefacts due to data inconsistencies given $[I=I_4^s]$ and $[I=I_1^e]$.

A single-line sub-revolution reconstruction is possible for reconstruction angle ranges from $\Delta \alpha_{q,min}$ through $\Delta \alpha_{q,max}$ with $$\Delta \alpha_{q,min} = \Pi + \beta_{fan} + \alpha_{trans} \qquad (26)$$

$$\Delta \alpha_{q,max} = 2\Pi \qquad (27).$$

$\beta_{fan}$ is the entire fan angle of the detector, $\alpha_{trans}$ is a selectable transition angle for reducing artefacts due to data inconsistencies between start and end projection of the reconstruction.

A single-line overscan reconstruction is possible for reconstruction angle ranges from $\Delta \alpha_{0,min}$ through $\Delta \alpha_{0,min}$ with $$\Delta \alpha_{0,min} = 2\Pi + 2\alpha_{tran} \qquad (28)$$

$$\Delta \alpha_{0,min} = 4\Pi \qquad (29).$$

A conventional overscan weighting is explained as an example.

$N_{RTD}$ projections are employed for the reconstruction; the number of projections per full revolution is $N_{2\Pi} \cdot N_{RTD} > N_{\Pi n}$ and $\Delta N_{RTD=NRTD} - N_{2n}$ then apply. The following weighting is undertaken then for calculating a single-line full revolution dataset $f_{2\Pi}(k,l)$ $$f_{2\pi}(k,l) = \begin{cases} S(l)f(k,l) + (1 - S(l))f(k, l + N_{2\pi}) & l = 1, 2, \ldots, \Delta N_{RTD} \\ f(k,l) & l = \Delta N_{RTD} + 1, \ldots, n_{2\pi} \end{cases} \qquad (30)$$

For example, S(I) can be employed as weighting function with $$\Delta N_{sub} = floor\left(\frac{\alpha_{trans}}{2\pi} N_{2\pi}\right).$$

$$s(l) = \begin{cases} 0.5\sin^2\left(\frac{\pi(l-1)}{2\Delta N_{sub}}\right) & l = 1, 2, \ldots \Delta N_{sub} \\ 0.5 & l = \Delta N_{sub} + 1, \ldots, \Delta N_{RTD} - \Delta N_{sub} \\ 0.5\left(1 + \sin^2\left(\frac{\pi(l - \Delta N_{RTD} + \Delta N_{sub} - 1)}{2\Delta N_{sub}}\right)\right) & l = \Delta N_{RTD} - \Delta N_{sub} + 1, \ldots, \Delta N_{RTD} \end{cases} \quad (31)$$

A good reduction of artifacts due to data inconsistencies in the start and end region of the projection angle interval utilized for the reconstruction is achieved with this "soft" transition weighting for adequately great $\alpha_{trans}$ (for example, $\alpha_{trans} > 8°$). As a result, the spiral interpolation which may be missing in the inventive spiral reconstruction method can be largely compensated. An overscan or sub-revolution reconstruction is realized in practically any commercially obtainable spiral CT apparatus; it therefore does not represent any added outlay.

The weighting methods are similar for a conventional sub-revolution reconstruction and need not be presented herein.

Figure 7:
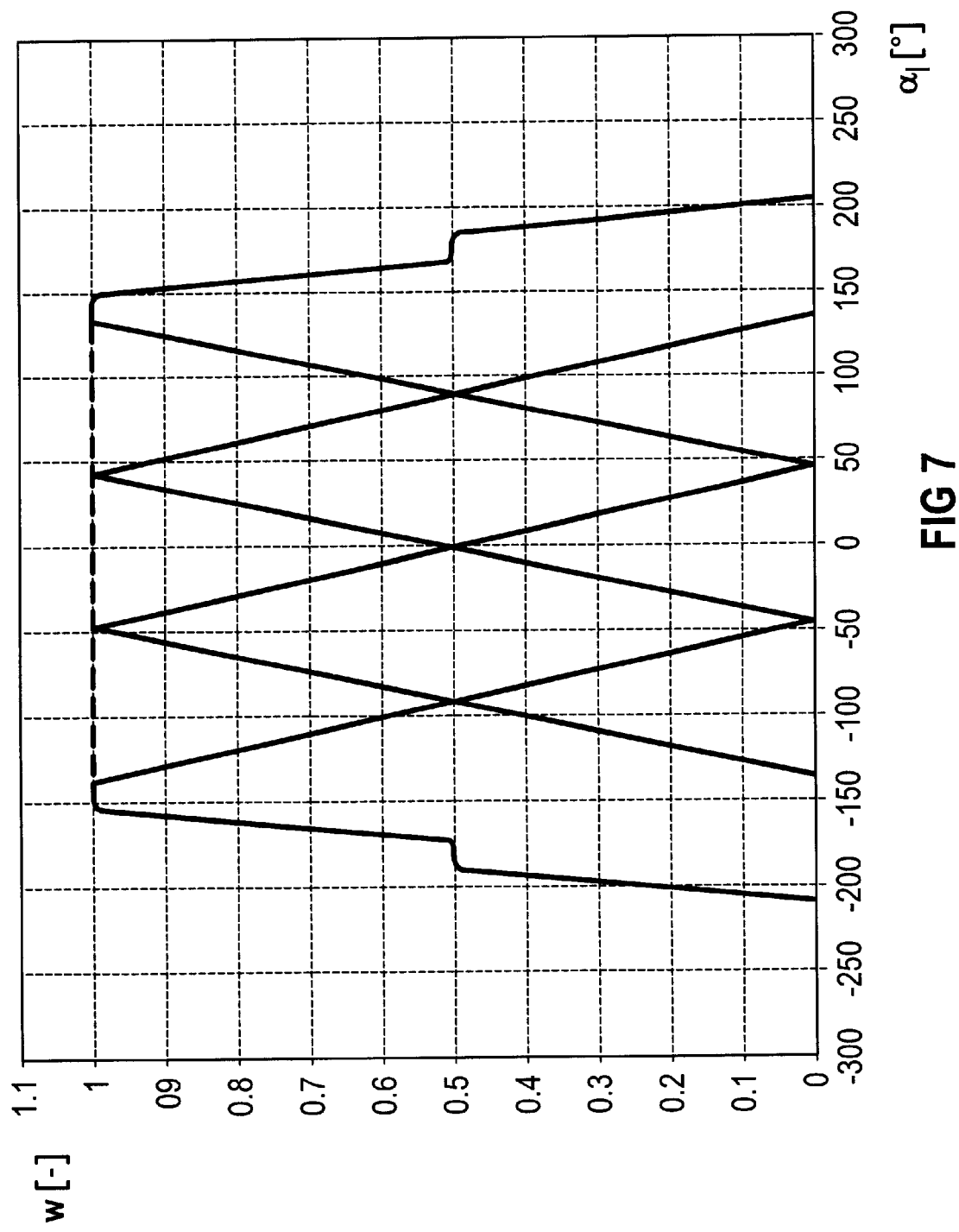
FIG. 7 is a diagram illustrating the effective weighting function resulting from the application of the weighting functions according to FIG. 6 as a function of the projection angle.

As an example of the combination of weighted addition of the measured values of the individual detector lines and subsequent sub-revolution or overscan weighting of the single-line data set that is produced, the "effective" weightings of the detector lines resulting therefrom for pitch 4 and $\alpha_{TRD} = 420°$ are shown in FIG. 7. An overscan having weightings according to "31" is assumed, namely with $\alpha_{trans} = 24°$. The broken line is the overall weighting of all four detector lines after spiral weighting and transition weighting. Of course, the transition weighting is not undertaken until after the spiral weighting.

Figure 8:
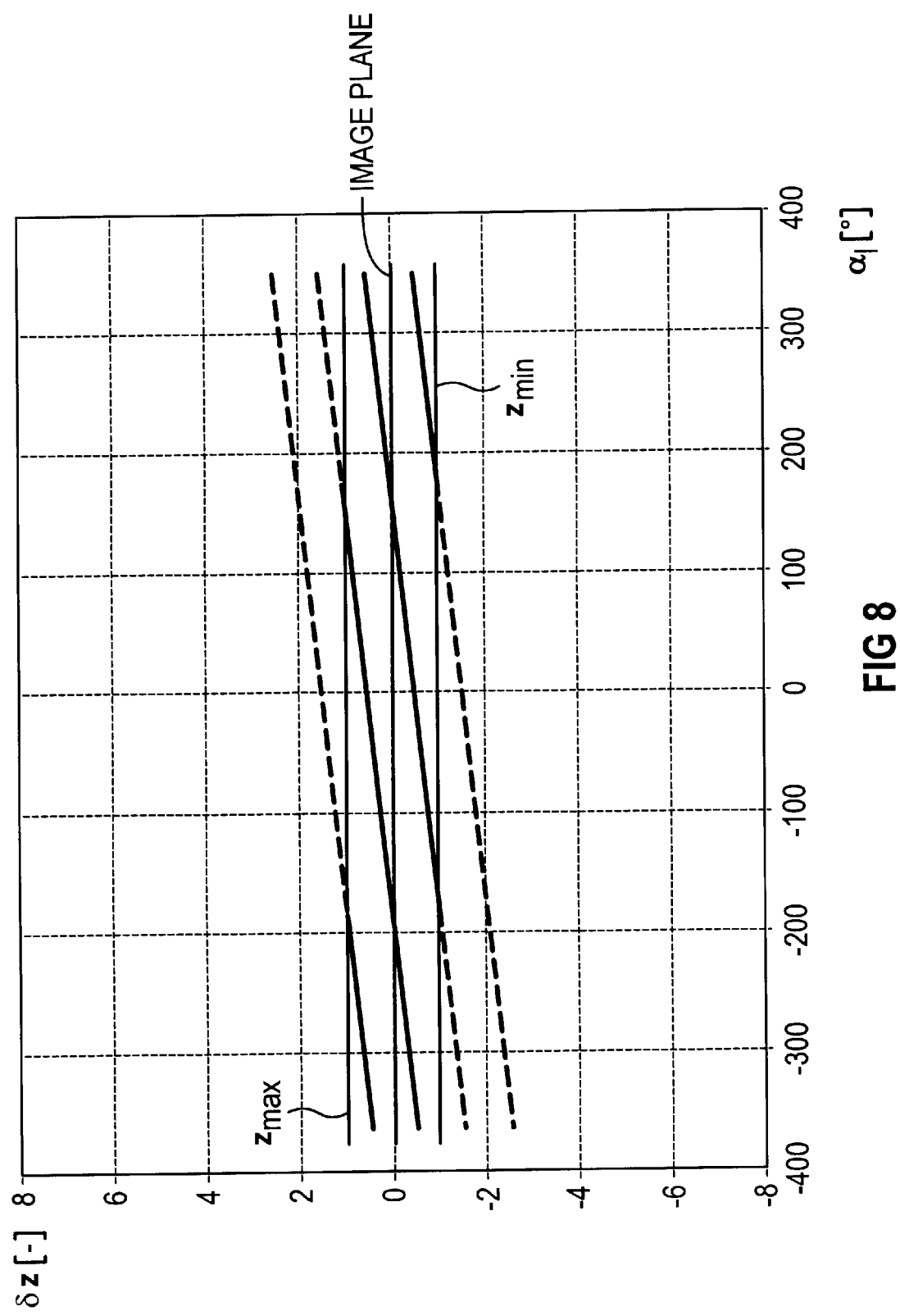
FIG. 8 is a diagram showing the distance of the detector lines of the spiral CT apparatus of FIG. 4 from the image plane normalized to the collimated slice thickness of detector line as function of the projection angle for a first pitch value.
Figure 9:
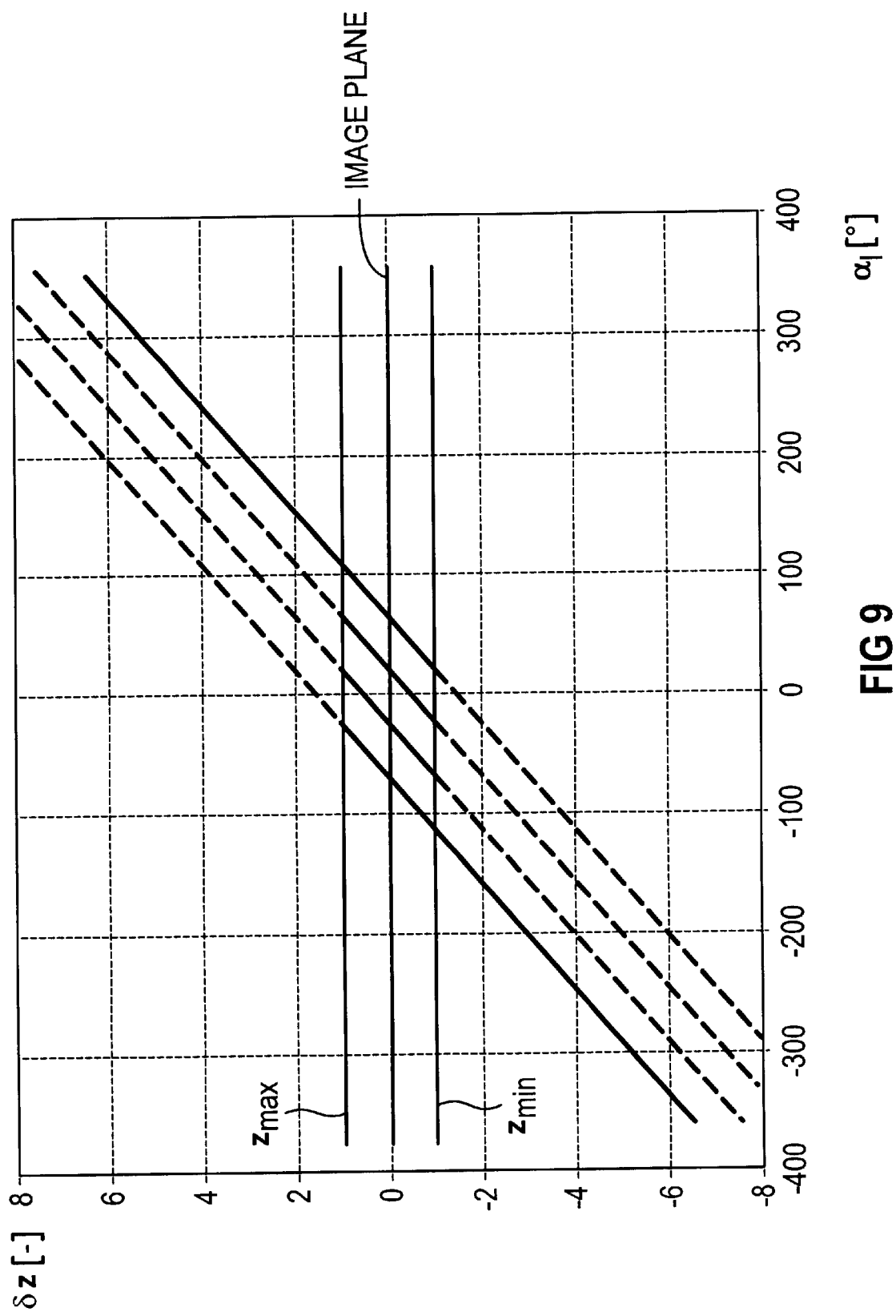
FIG. 9 is in an illustration analogous to FIG. 8, showing the relationships for a second pitch value.

With increasing pitch p, the M detector lines move more rapidly through the z-interval $[z_{ima} - \Delta z, z_{ima} + \Delta z]$. As a consequence, the projection angle range $\alpha_{TRD}$ for which at least one of the four detector lines lies in the range $[z_{ima} - \Delta z, z_{ima} + \Delta z]$ for every projection angle $\alpha_1$ becomes narrower. This is shown in FIG. 8 in which the distance of the M=4 detector lines from the image plane given $z_{ima} = 0$ for pitch p=1 normalized to the collimated width d of a line of detector elements of the detector, i.e. the collimated slice thickness, is entered as function of the projection angle $\alpha_1$ for $-360° \leq \alpha_1 \leq 360°$. For each $\alpha_1$, at least one line lies closer to the image plane than $\Delta z$. Without degrading the slice sensitivity profile, an overscan is therefore possible in the maximum projection angle range $\alpha_{TRD} = 720°$ and, of course, in every smaller projection angle range as well, this being an excerpt from the maximum range shown in FIG. 8. FIG. 9 shows the normalized distance of the four lines from the image plane given the pitch 8. Theoretically, an overscan reconstruction with $\alpha_{TRD} = 720°$ could also be implemented here. According to (21) and (24), however, the weightings $w_4(I) = 1$ and $w_1(I) = 1$ would have to be allocated respectively to the lines 4 and 1 for large angular ranges ($-360° \leq \alpha_1 \leq -120°$ for line 4 and $120° \leq \alpha_1 \leq 360°$ for line 1). As a result, the slice sensitivity profile would considerably broaden and the image quality would suffer. Instead, a usable selection for pitch p=8 is a sub-revolution reconstruction in the angular range $\alpha_{TRD} = 240°$.

In general, the angular segment $\alpha_{TRD}$ contributing to the reconstruction can be selected greater with decreasing pitch p. Given pitch p=1, for example, each reconstruction angular range $\alpha_{TRD}$ —as shown above—is possible with $\alpha_{q,min} \approx 240° \leq \alpha_{RTD} \leq \Delta\alpha_{o,max} = 720°$ without degrading the slice sensitivity profile. When $\alpha_{TRD}$ becomes larger, however, more measuring rays contribute to the image and thus more x-ray quanta contribute; and, given an established output power of the x-ray tube, the pixel noise becomes lower. Enlarging $\alpha_{TRD}$, however, is equivalent to lengthening the time interval from which the measured data derive, and thus a diminishment of the time resolution of the reconstruction. Conversely, a diminution of $\alpha_{TRD}$ is accompanied by a deterioration of the dose utilization but also by an improvement of the time resolution as can be meaningful, for example, for specific exposures of moving objections (lung, heart). The possibility of a freely selectable compromise between dose utilization and time resolution does not exist given the standard 180LI or 360LI interpolation; it is a critical advantage of the inventive method.

Figure 1:
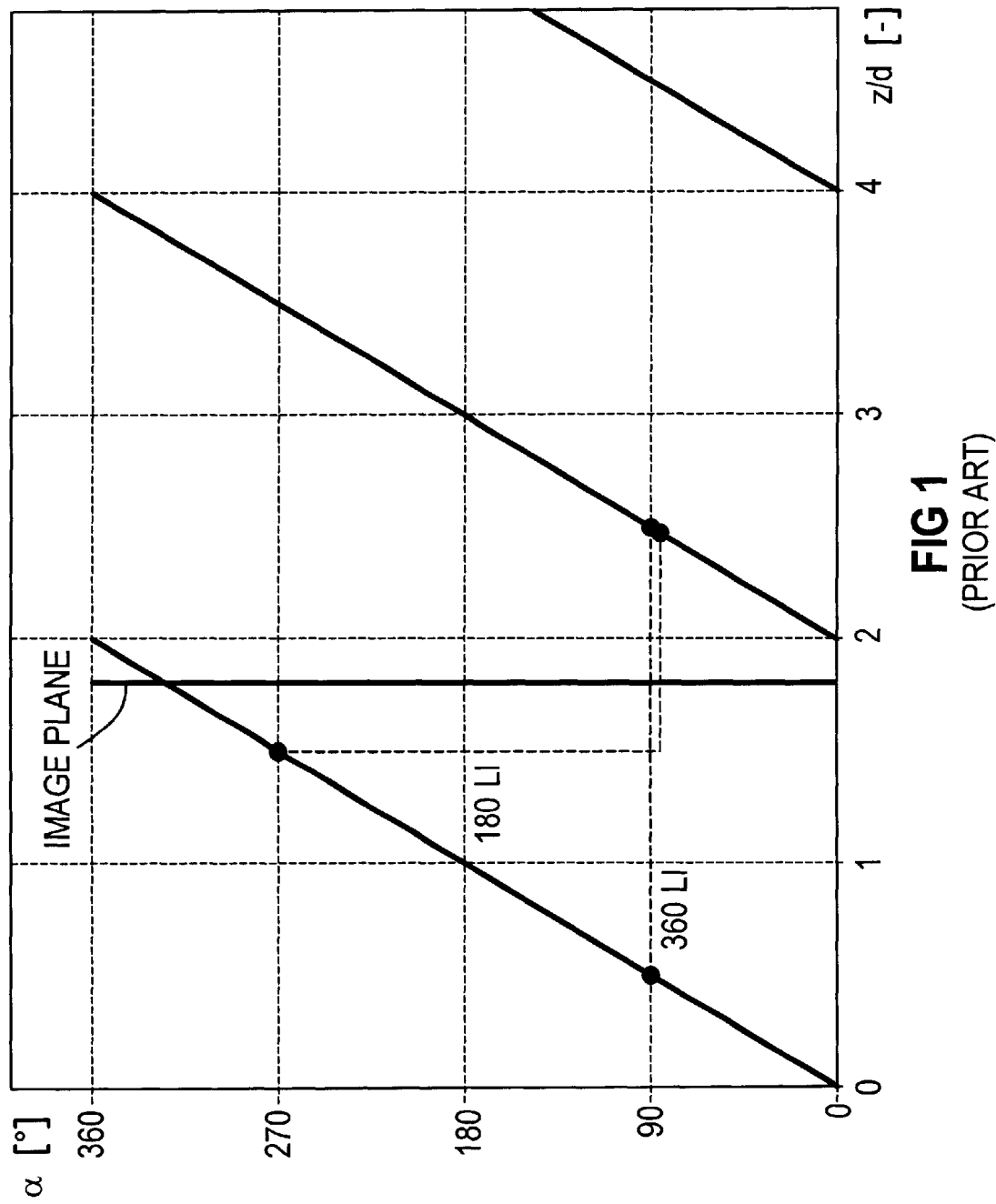
FIG. 1 is a diagram of a spiral CT apparatus having a detector with a single line of detector elements, illustrating the projection angle as function of the detector position in the z-direction during a spiral scan.
Figure 2:
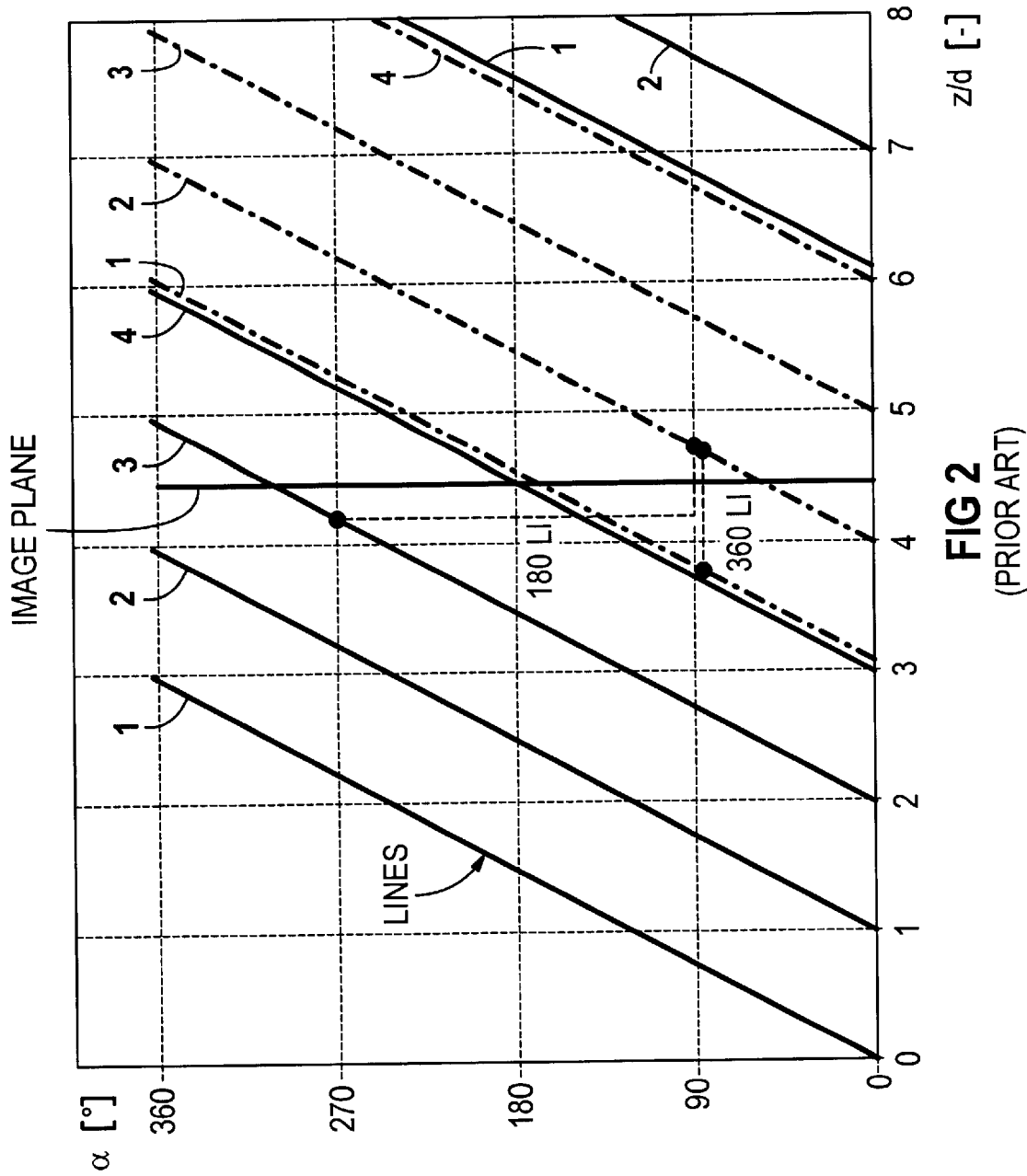
FIG. 2 is an illustration analogous to FIG. 1, which shows the relationships for a spiral CT apparatus with a detector having four lines of detector elements.
Figure 3:
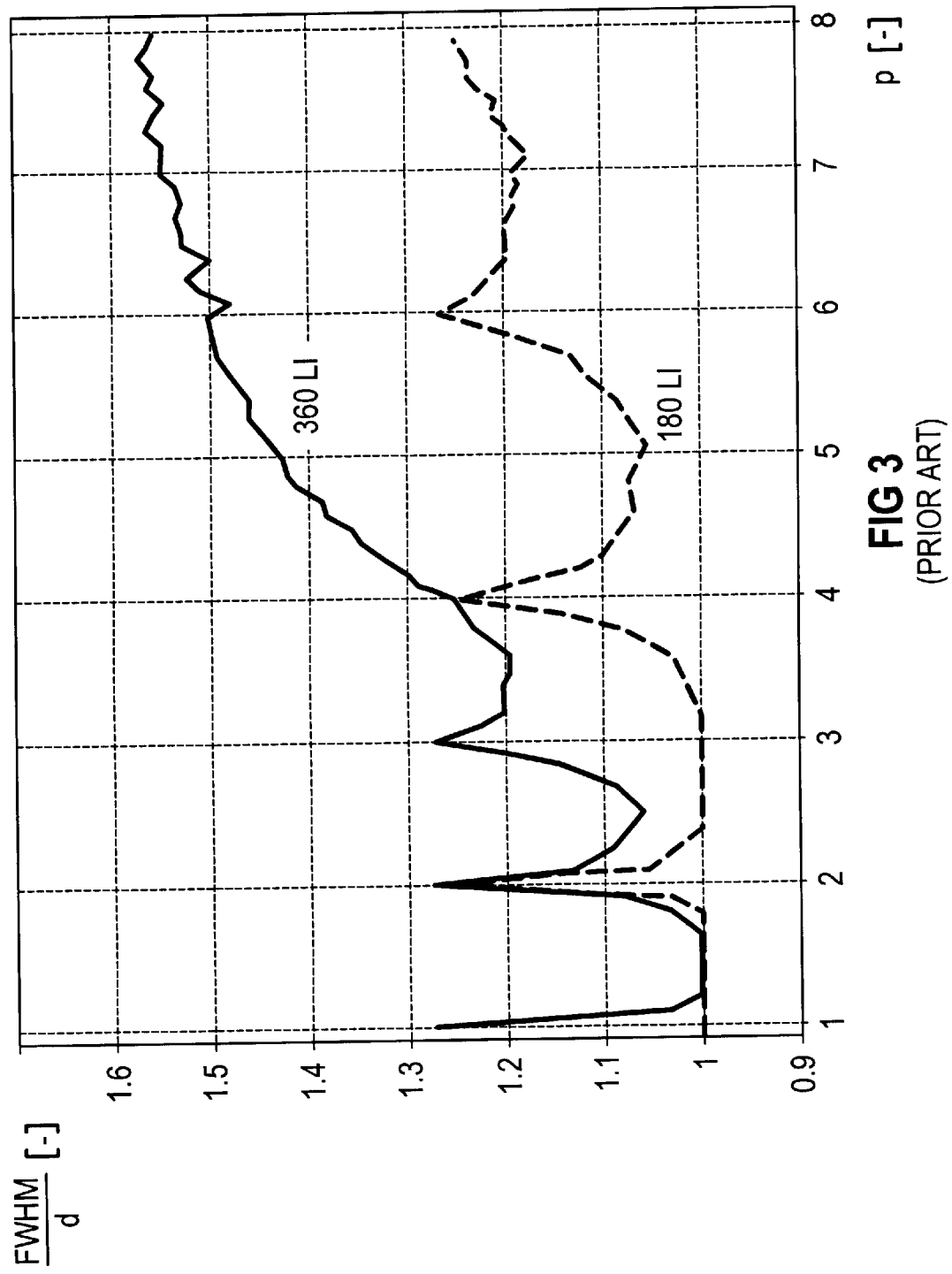
FIG. 3 is a diagram showing the full width at half-maximum of the slice sensitivity profile dependent on the pitch for the 360 LI and 180 LI interpolation for a spiral CT apparatus with a detector having four lines of detector elements.
Figure 10:
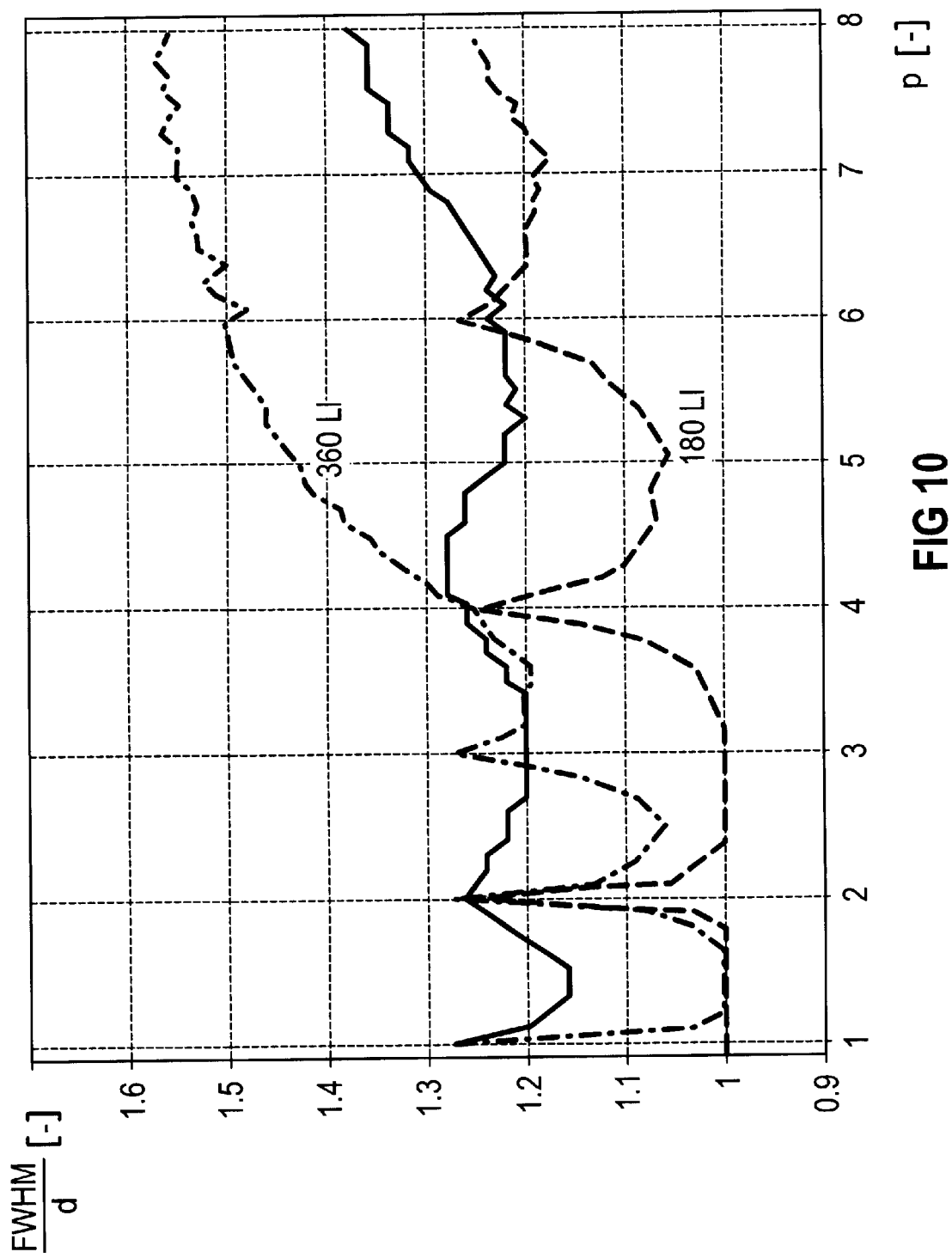
FIG. 10 shows the full wave at half-maximum of the slice sensitivity profile for the spiral CT apparatus according to FIG. 4 with a detector having four lines of detector elements, as function of the pitch value.

As an example, FIG. 10 shows the full width at half-maximum (FWHM) of the slice sensitivity profile for a picture element in the region of the z-axis for the inventive method for a 4-line detector (M=4) as function of the pitch value p in the range $1 \leq p \leq 8$. A 420° overscan reconstruction was selected for $1 \leq p \leq 2$ and a 240° sub-revolution reconstruction was selected for $2 \leq p \leq 8$. $\alpha_{trans} = 8°$ applies in both instances. The half-maximums that derive in the standard 180LI or 360LI interpolations are also entered (See FIG. 3). Although the calculating outlay for a complementary interpolation is avoided in the case of the inventive method in the range $4 \leq p \leq 8$, the slice sensitivity profile is clearly narrower than given a standard 360LI interpolation.

The inventive method allows the reconstruction of images from spiral data sets even given non-constant relative motion in z-direction, for example given a periodic cosine-shaped back and forth motion.

The spiral weighting of the projections of the M detector lines thus sequences as follows for that case wherein an image is to be reconstructed at the z-position $z_{ima}$:

As a result of the spiral weighting, a single-line data set is produced that is supplied to a regular overscan or sub-revolution reconstruction in the freely selectable angular range $\Delta\alpha = \alpha_{RTD}$. $N_{RTD}$ multi-line projections are thereby used. In every projection I, let the z-position ($z_i(I)$) be established for each of the M detector lines i=1,2, . . . ,M.

Let $I^{ima}$ be that M-line projection for which the path of the focus intersects the image plane.

Those detector lines i for whose distance from the image plane $$|\delta z_i(I)| = |z_i(I) - z_{ima}| \leq \Delta z \quad (32)$$

applies are now determined for each projection I in the entire projection angular range $$\left[I^{ima} - \frac{N_{RTD}}{2}, I^{ima} + \frac{N_{RTD}}{2} - 1\right].$$

The measured values of these lines are then weighted and added according to their distance from the image plane.

For the simple case Hz=1, at most two lines i and i+1 contribute to the image for each projection angle $\alpha$.

$$w_i(I) = 1 - |\delta z_i(I)|$$

$$w_{i+1}(I) = 1 - |\delta z_{i+1}(I)| = 1 - w_i(I) \tag{33}$$

is then valid given two lines with linear weighting.

Figure 11:
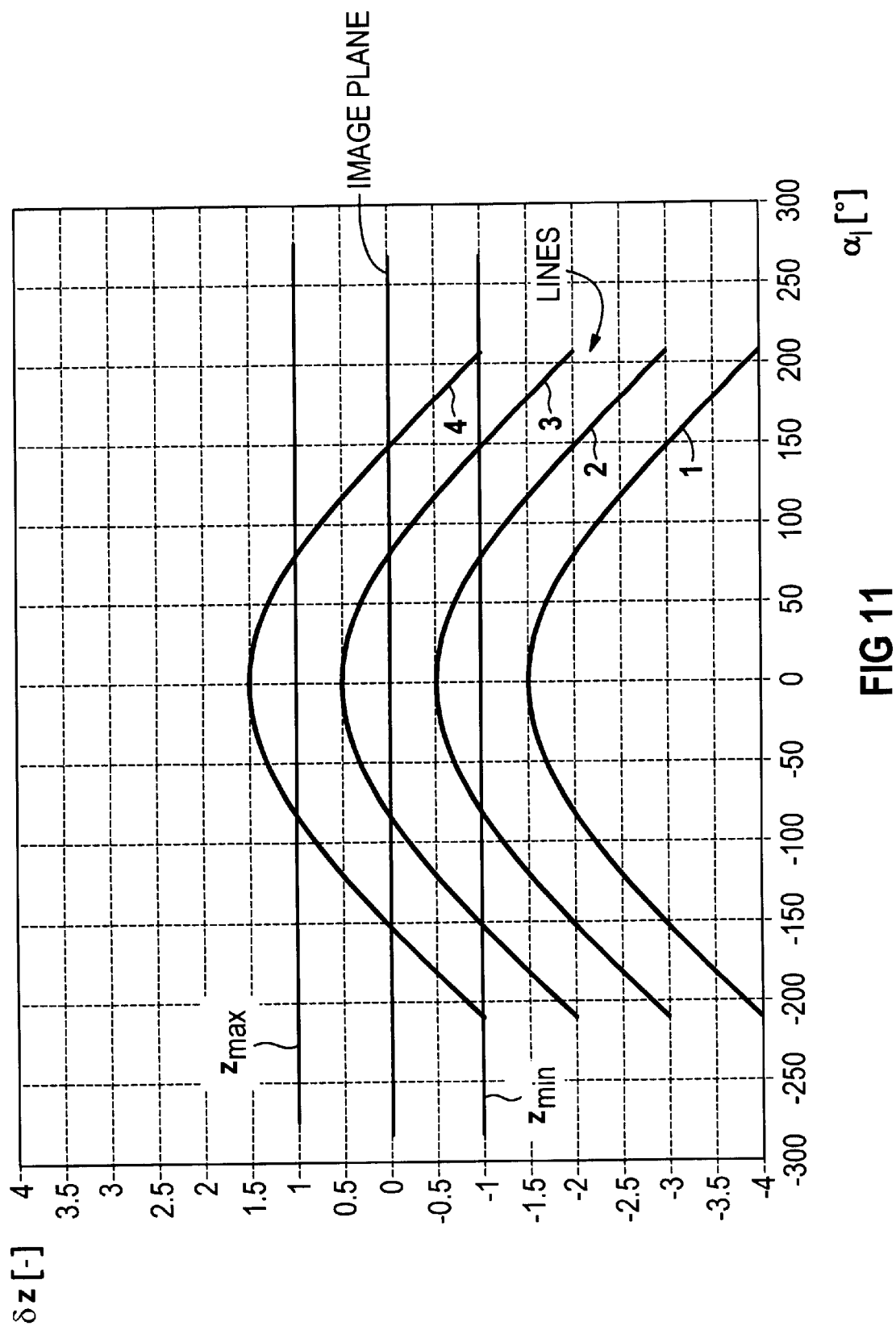
FIG. 11 is a diagram illustrating the inventive, weighted combination of the measured values for the spiral CT apparatus according to FIG. 4 given a non-constant, cosine-shaped relative motion between the examination subject, and the radiation source and detector.
Figure 12:
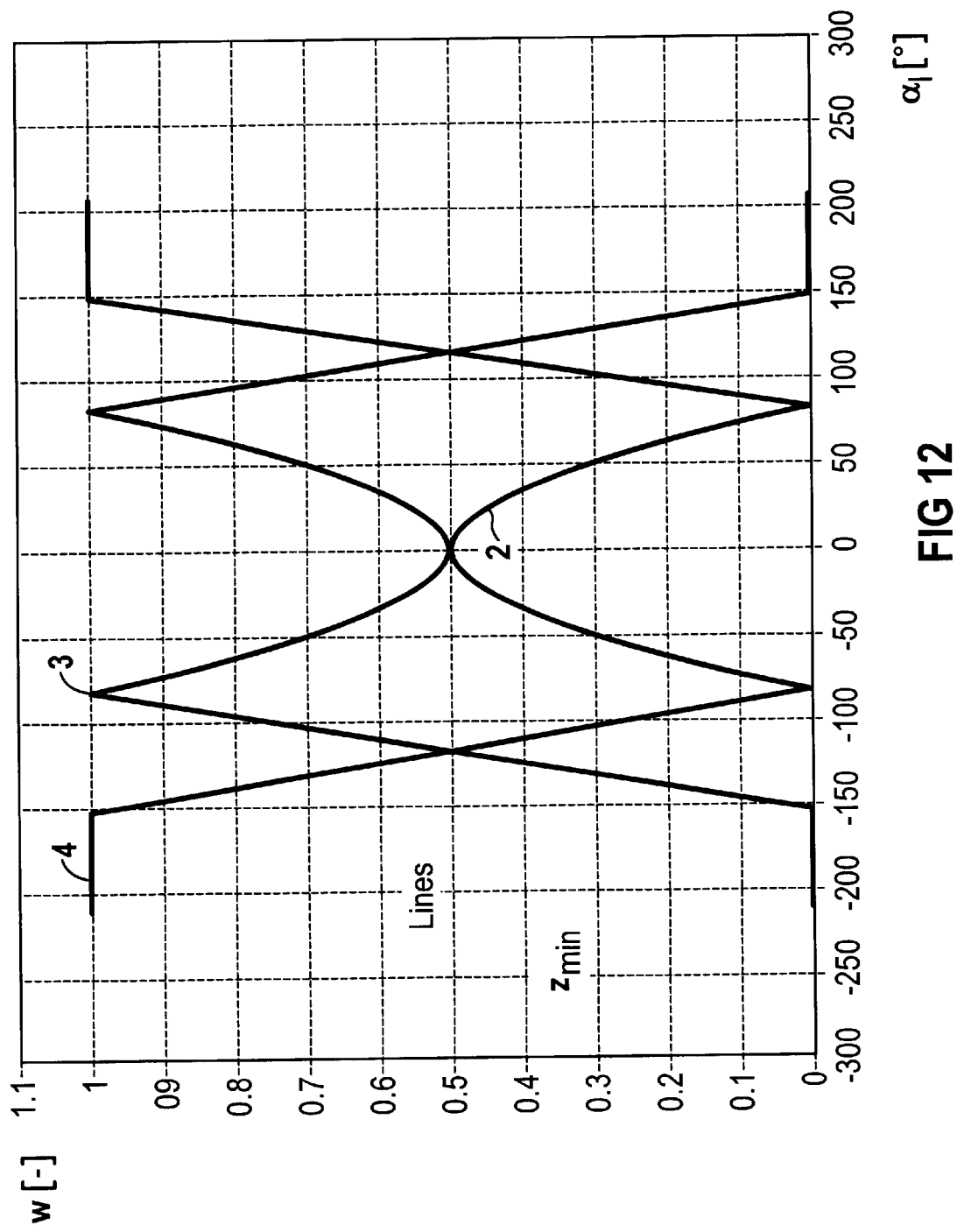
FIG. 12 is a diagram showing the weighting functions to be applied for the individual lines of detector elements in the combination of the measured values according to FIG. 11 dependent on the projection angle.

As an example of non-constant table feed, the z-position of the central channels of the individual lines of a 4-line detector is shown in FIG. 11 as function of the projection angle $\alpha$ (also see FIG. 5). When one wishes to implement an overscan reconstruction in the overall angular range $\Delta\alpha = \alpha_{over} = 420°$ for FIG. 5, the weighting functions for the M=4 detector lines entered in FIG. 12 derive with $\Delta z = 1$ and with linear weighting (also see FIG. 6).

The inventive method was explained above with reference to the example of a CT apparatus of the third generation, however, it can also be employed for a CT apparatus of the fourth generation.

The number of lines of the detector provided in the case of the exemplary embodiment is to be understood as being only by way of example.

The inventive method can be employed not only in the medical field as in the exemplary embodiment. Applications in the non-medical field are also within the scope of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for image reconstruction in a spiral computed tomography apparatus comprising a radiation source having a focus from which a fan-shaped X-ray beam emanates, at least said focus being movable around a system axis around an examination subject, and a detector comprising a plurality of lines of detector elements which receive the fan-shaped X-ray beam, the examination subject and the radiation source plus the detector being displaceable relative to one another in the direction of the system axis, while rotating said focus around said system axis, for the conducting of an examination, said method comprising the steps of:

(a) registering a plurality of projections using a respective plurality of said lines of detector elements for a plurality of projection angles and positions along the system axis, with the same lines of detector elements being employed for the registration of all projections;

(b) acquiring measured values for an image reconstruction of an image plane at a specific position on the system axis by combining projections, respectively comprising measured values, for each individual projection angle needed for this image reconstruction, that are registered exclusively for this projection angle with different lines of detector elements, to form data apparently registered with a detector comprising only one line of detector elements, by weighting the measured values respectively acquired by different lines of detector elements, dependent on a distance of the line of detector elements, from which the respective measured values were acquired, from the image plane in the direction of the system axis and without using a channel angle of the individual detector elements of said line of detector elements from which the measured values were acquired; and (c) conducting said image reconstruction by subjecting said data to an algorithm for reconstructing an image from a detector comprising only one line of detector elements.

2. A method as claimed in claim 1, wherein step (c) comprises conducting the image reconstruction as a sub-revolution reconstruction employing only data corresponding to a partial revolution of the radiation source around the system axis through a revolution angle minimally required for the image reconstruction.

3. A method as claimed in claim 1, wherein step (c) comprises conducting the image reconstruction as an overscan reconstruction employing more data than correspond to a partial revolution of the radiation source around the system axis with a revolution angle minimally required for the image reconstruction.

4. A method as claimed in claim 1, wherein step (b) comprises combining the data sequentially for the projection angles needed for the image reconstruction.

5. A method as claimed in claim 1, wherein step (b) comprises suppressing combinations of direct and complementary measured values when combining the data for the projection angles needed for the image reconstruction.

6. A method as claimed in claim 1 wherein weighting the measured values respectively acquired by different lines of detector elements dependent on a distance of the line of detector elements, from which the respective measured values were acquired, from the image plane in the direction of the system axis comprises weighting said measured values with respectively increasing weights as said distance of the line of detector elements, from which the respective measured values were acquired, from the image plane in the direction of the system axis decreases.

7. A spiral computed tomography apparatus comprising:

a radiation source having a focus from which a fan-shaped X-ray beam emanates, at least said focus being movable around a system axis around an examination subject;

a detector comprising a plurality of lines of detector elements which receive the fan-shaped X-ray beam;

means for effecting a relative displacement between the examination subject and the radiation source plus the detector, in the direction of the system axis, while rotating said focus around said system axis, for conducting an examination; and a parallel computer which controls said X-ray source and said detector and said means for displacing, for registering a plurality of projections using a respective plurality of said lines of detector elements for a plurality of projection angles and positions along said system axis, with the same lines of detector elements being employed for the registration of all projections, and for acquiring measured values for an image reconstruction of an image plane at a specific position on the system axis by combining projections, respectively comprising measured values, for each individual projection angle needed for this image reconstruction, that are registered exclusively for this projection angle with different lines of detector elements, to form data apparently registered by a detector comprising only one line of detector elements, by weighting the measured values respectively acquired by different detector lines of detector elements, dependent on a distance of the line of detector elements, from which the respective measured values were acquired, from the image plane in the direction of the system axis and independent of a channel angle of the individual detector elements of said line from which the respective measured values were acquired, and conducting said image reconstruction by subjecting said data to an algorithm for reconstructing an image from a detector comprising only one line of detector elements.

8. A spiral computed tomography apparatus as claimed in claim 7 wherein said computer suppresses combinations of direct and complementary measured values when combining the data for the projection angles needed for the image reconstruction.

9. A spiral computed tomography apparatus as claimed in claim 7 further comprising an input unit for supplying inputs to said parallel computer allowing a free selection of a region of the projection angles needed for the image reconstruction.

10. A spiral computed tomography apparatus as claimed in claim 7 wherein said parallel computer controls said means for displacing so as to produce a relative motion between said examination subject, and said radiation source plus said detector, with at least one of a variable direction and a variable speed.

11. A spiral computed tomography apparatus as claimed in claim 10 wherein said parallel computer controls said means for displacing to produce a back and forth relative motion between said examination subject, and said radiation source plus said detector, along said system axis.

12. A spiral computed tomography apparatus as claimed in claim 10 further comprising an input unit, connected to said parallel computer, for supplying inputs to said parallel computer for freely selecting a region of said projection angles needed for said image reconstruction.

13. A spiral computed tomography apparatus as claimed in claim 7 wherein said computer sequentially combines the data for the projection angles needed for the image reconstruction.

14. A spiral computed tomography apparatus as claimed in claim 7 wherein the parallel computer weights the measured values respectively acquired by different lines of detector elements dependent on a distance of the line of detector elements, from which the respective measured values were acquired, from the image plane in the direction of the system axis, by weighting said measured values with respectively increasing weights as said distance of the line of detector elements, from which the respective measured values were acquired, from the image plane in the direction of the system axis decreases.

15. A spiral computed tomography apparatus comprising:
a radiation source having a focus from which a fan-shaped X-ray beam emanates, at least said focus being movable around a system axis around an examination subject;
a detector comprising a plurality of lines of detector elements which receive the fan-shaped X-ray beam;
means for effecting a relative displacement between the examination subject and the radiation source plus the detector, in the direction of the system axis, while rotating said focus around said system axis, for conducting an examination; and
a computer which controls said X-ray source and said detector and said means for displacing, for registering a plurality of projections using a respective plurality of said lines of detector elements for a plurality of projection angles and positions along said system axis, with the same lines of detector elements being employed for the registration of all projections, and for acquiring measured values for an image reconstruction of an image plane at a specific position on the system axis by combining projections, respectively comprising measured values, for each individual projection angle needed for this image reconstruction, that are registered exclusively for this projection angle with different lines of detector elements, to form data apparently registered by a detector comprising only one line of detector elements, by weighting the measured values respectively acquired by different detector lines of detector elements, dependent on a distance of the line of detector elements, from which the respective measured values were acquired, from the image plane in the direction of the system axis and independent of a channel angle of the individual detector elements of said line from which the respective measured values were acquired, and conducting said image reconstruction by subjecting said data to an algorithm for reconstructing an image from a detector comprising only one line of detector elements.

16. A spiral computed tomography apparatus as claimed in claim 15 wherein said computer suppresses combinations of direct and complementary measured values when combining the data for the projection angles needed for the image reconstruction.

17. A spiral computed tomography apparatus as claimed in claim 15 further comprising an input unit for supplying inputs to said computer allowing a free selection of a region of the projection angles needed for the image reconstruction.

18. A spiral computed tomography apparatus as claimed in claim 15 wherein said computer controls said means for displacing so as to produce a relative motion between said examination subject, and said radiation source plus said detector, with at least one of a variable direction and a variable speed.

19. A spiral computed tomography apparatus as claimed in claim 18 wherein said computer controls said means for displacing to produce a back and forth relative motion between said examination subject, and said radiation source plus said detector, along said system axis.

20. A spiral computed tomography apparatus as claimed in claim 18 further comprising an input unit, connected to said computer, for supplying inputs to said computer for freely selecting a region of said projection angles needed for said image reconstruction.

21. A spiral computed tomography apparatus as claimed in claim 18 wherein the computer weights the measured values respectively acquired by different lines of detector elements dependent on a distance of the line of detector elements, from which the respective measured values were acquired, from the image plane in the direction of the system axis, by weighting said measured values with respectively increasing weights as said distance of the line of detector elements, from which the respective measured values were acquired, from the image plane in the direction of the system axis decreases.

22. A spiral computed tomography apparatus as claimed in claim 15, wherein said computer sequentially combines the data for the projection angles needed for the image reconstruction.

23. A computed tomography apparatus comprising
a radiation source having a focus from which a fan-shaped X-ray beam emanates, at least said focus being movable around a system axis around an examination subject;
a detector comprising a plurality of lines of detector elements which receive the fan-shaped X-ray beam;
means for effecting a relative displacement between the examination subject and the radiation source plus the detector, in the direction of the system axis for conducting an examination; and
a parallel computer which controls said X-ray source and said detector and said means for displacing, for registering a plurality of projections using a respective plurality of said lines of detector elements for a plurality of projection angles and positions along said system axis, with the same lines of detector elements being employed for the registration of all projections, and for acquiring measured values for an image reconstruction of an image plane at a specific position on the system axis by combining projections, respectively comprising measured values, for each individual projection angle needed for this image reconstruction, that are registered exclusively for this projection angle with different lines of detector elements, to form data apparently registered by a detector comprising only one line of detector elements, by weighting the measured values respectively acquired by different detector lines of detector elements, dependent on a distance of the line of detector elements, from which the respective measured values were acquired, from the image plane in the direction of the system axis and independent of a channel angle of the individual detector elements of said line from which the respective measured values were acquired, and conducting said image reconstruction by subjecting said data to an algorithm for reconstructing an image from a detector comprising only one line of detector elements.

24. A computed tomography apparatus as claimed in claim 23 wherein the parallel computer weights the measured values respectively acquired by different lines of detector elements dependent on a distance of the line of detector elements, from which the respective measured values were acquired, from the image plane in the direction of the system axis, by weighting said measured values with respectively increasing weights as said distance of the line of detector elements, from which the respective measured values were acquired, from the image plane in the direction of the system axis decreases.

* * * * *